United States Patent [19]

Ellis et al.

[11] Patent Number: 5,783,741
[45] Date of Patent: Jul. 21, 1998

[54] CAPILLARY FURNACE FOR IMPROVED PEAK RESOLUTION IN GAS ISOTOPE CHROMATOGRAPHY

[75] Inventors: Leroy Ellis; Ann L. Fincannon, both of Plano, Tex.

[73] Assignee: Atlantic Richfield Company, Los Angeles, Calif.

[21] Appl. No.: 791,216

[22] Filed: Jan. 31, 1997

[51] Int. Cl.$^6$ .......................... B01D 15/08; B01D 59/44; H01J 49/04; G01N 30/08
[52] U.S. Cl. .......................... 73/23.39; 73/23.42; 55/197; 55/386; 422/89; 436/161; 250/288
[58] Field of Search .................. 73/23.39, 23.35, 73/23.42; 55/197, 386; 422/89; 436/161, 159; 250/288

[56] References Cited

U.S. PATENT DOCUMENTS

| | | | |
|---|---|---|---|
| 3,457,773 | 7/1969 | Villalobos | 73/23.1 |
| 4,805,441 | 2/1989 | Sides et al. | 73/23.1 |
| 4,866,270 | 9/1989 | Hall et al. | 250/282 |
| 4,916,313 | 4/1990 | Hall et al. | 250/282 |
| 5,012,052 | 4/1991 | Hayes | 250/288 |
| 5,141,534 | 8/1992 | Sacks et al. | 55/197 |
| 5,314,827 | 5/1994 | Schmidt et al. | 436/106 |
| 5,424,539 | 6/1995 | Brand et al. | 250/288 |
| 5,437,179 | 8/1995 | Wiegand et al. | 73/23.35 |
| 5,547,497 | 8/1996 | Klemp et al. | 96/104 |

*Primary Examiner*—Hezron E. Williams
*Assistant Examiner*—J. David Wiggins
*Attorney, Agent, or Firm*—Drude Faulconer

[57] ABSTRACT

An isotope ratio monitoring gas chromatograph-mass spectrometer (irm-GC/MS) unit for generating a chromatogram having improved resolution for peaks representative of individual carbon dioxide isotopes measured when a complex GC amenable organic sample (e.g. petroleum hydrocarbons) is combusted in the presence of a metal catalyst. The present irm-GC/MS unit is similar to known irm-GC/MS units of this type except it uses a capillary combustion tube in the furnace which is connected to the capillary column and has approximately the same inside diameter as that of the capillary column (e.g. 0.25 mm I.D.) whereby any "dead volume" attributable to the combustion tube is substantially eliminated.

15 Claims, 2 Drawing Sheets

CAPILLARY FURNACE FOR IMPROVED PEAK RESOLUTION IN GAS ISOTOPE CHROMATOGRAPHY

DESCRIPTION

1. Technical Field

The present invention relates to an isotope ratio monitoring gas chromatograph-mass spectrometer (irm-GC/MS) unit having a capillary isotope furnace and in one of its aspects relates an irm-GC/MS unit for measuring the isotopes of carbon dioxide resulting from combustion of a a GC amenable organic sample wherein "dead volume" within the carrier gas flowpath is substantially reduced by using a capillary tube as the flowpath through the combustion reactor (i.e. furnace) thereby improving peaks resolution on the chromatographic trace.

2. Background Art

Gas chromatography (GC) is widely-used for isolating, separating, and measuring the components of GC amenable complex mixtures. These measurements are then used to determine certain chemical and physical properties and/or characteristics of the various components and/or of the mixture, itself. For example, specialized GC methodologies are commonly used for measuring and determining various properties or characteristics of individual hydrocarbon components (e.g. methane, ethane, propane, etc.) which make up a particular hydrocarbon gas or mixture.

One such commonly-used application employs an isotope ratio monitoring gas chromatograph-mas spectrometer ("irm-GC/MS") to detect and measure the different isotopes of carbon dioxide which are generated when the respective hydrocarbon components (e.g. methane, ethane, propane, etc.) of a hydrocarbon mixture undergo combustion in the presence of a metal catalyst (e.g. copper, nickel, and/or platinum). With proper analysis and inspection of these measurements, certain geochemical and other desired characteristics of that particular hydrocarbon mixture can be determined; e.g. the source of said hydrocarbons, how they were formed, etc.

Typical irm-GC-MS systems used in the detection of organic isotopes are generally comprised of a polyimide-coated capillary column in a variable heating oven (i.e. gas chromatograph), a combustion reactor (sometimes referred to as a "furnace"), a water separator, a gas reduction unit, an isotope ratio mass spectrometer, and a data processing unit. As will be readily understood in this art, a sample of a particular GC amenable mixture is injected into the column where it is heated (e.g. to approximately 300° C.) to "distill" and separate the various components of the mixture. As the components are vaporized, they are transported via a carrier gas (nitrogen or helium) from the capillary column into the combustion reactor or furnace where the temperature is approximately 900° C. In the presence of a metal catalyst (e.g. copper, nickel, and/or platinum) at these elevated temperatures, these volatile organic components are converted into their respective carbon dioxide and water products.

As will be understood in the art, the water and any excess carbon dioxide which might otherwise overload the detector electronics of the mass spectrometer are required to be removed from the sample stream before it is passed through the mass spectrometer. The mass spectrometer separately detects and measures each respective carbon dioxide isotope as that gas flows therethrough and generates a signal representative thereof. The respective signals are then processed to produce a chromatograph trace illustrating a curve with "peaks" thereon which, in turn, are representative of the respective carbon dioxide isotopes in the sample.

These measurements are further processed to generate numerical data (e.g. the area under the peaks are integrated) which, in turn, are then interpreted in accordance with known relationships to arrive at the desired information about the sampled hydrocarbon mixture. Again, this basic data processing procedure is commonly used and is well known in the art.

As will be appreciated by those working in this art and in any such irm-GC/ms operation, "peak" resolution is essential in achieving accurate carbon dioxide isotope measurements from a particular sample. That is, the "sharper" the peak on the chromatograph trace, the more accurate the measurement of that particular carbon dioxide isotope signature (i.e. area under the peak) will be since the exact points along curve on the chromatograph trace at which a particular peak begins and ends (i.e. the points between which the curve is to be integrated) can be more readily identified.

Unfortunately, in known irm-GC/MS systems of this type, the peaks on the chromatographic trace are generally broader at their base which may obscure the start and end points of closely eluting (i.e. spaced) peaks in complex mixtures. This broadening of the peaks appears to result from a slowing of the carrier gas flow within the sample flowpath wherein at least a few of the carbon dioxide isotopes of one hydrocarbon component, e.g. methane, which should be shown under the "methane" peak are delayed and are detected as part of the next group of carbon dioxide isotopes and accordingly may be erroneously shown under the "ethane" peak. While these errors may appear to be small, they, nevertheless, generate significant errors in the precise calculations ultimately made from these measurements.

It is believed that this "slowing" of the sample flow through the irm-GC/MS unit is caused, at least in part, by "dead volume" which may be present in the flowpath. This dead volume may occur at any point in the path where the volume of the flowpath increases, e.g. at connections along the flow path, etc. As the sample encounters "dead volume" along the flowpath, the back pressure on the sample decreases and, flow slows as the sample expands into the additional space available (i.e. dead volume). In known irm-GC/MS systems of the type used to measure hydrocarbon isotopes, substantial dead volume normally occurs in the flowpath as it passes through the combustion reactor or furnace.

Furnaces used in prior art irm-GC/MS systems generally use a larger diameter glass or ceramic tube (e.g. 0.6 mm inner diameter "ID") to form the sample flowpath therethrough. This relatively large diameter tube is connected directly to the GC column which, in turn, is a small, capillary tube, e.g. approximately 0.25 mm. diameter. The connection of the large tube in the furnace to the capillary tube of the GC column, may result in the creation of a relatively large dead volume that has been shown to severely affect the final results of the carbon dioxide isotope measurements as reflected by broader peaks on the chromatograph trace. Accordingly, improvements are needed in the sample flowpath to eliminate dead volume therefrom to thereby improve the sharpness and resolution of the peaks on the chromatograph trace.

SUMMARY OF THE INVENTION

The present invention relates to an improved isotope ratio monitoring gas chromatograph-mass spectrometer (irm-GC/

MS) unit which is capable of measuring the individual carbon dioxide isotopes produced when respective components (e.g. methane, ethane, etc.) of a complex GC amenable organic sample (e.g. petroleum hydrocarbons) are combusted in the present of a metal catalyst and then generating a chromatographic trace or chromatogram having peaks thereon representative of the measured isotopes. The present irm-GC/MS unit is similar to known irm-GC/MS units of this type in that it is comprised of a gas chromatograph (GC), a combustion reactor or furnace, a water separator, a gas-reduction unit, a mass spectrometer (MS), and a data processing unit. Each of these components include a flowpath which, when connected, form a continuous flowpath for the sample between the GC and the MS.

As will be understood, the components of this type of irm-GC-MS units are fairly standard and well known in the art. For example, the GC used in irm-GC-MS units of this type is typically comprised of a capillary column which, in turn, is formed of a coiled-length of polyimide-coated, glass capillary tubing (e.g. 0.25 mm I.D.) positioned within an oven. A sample, injected into the column, will be heated within the oven wherein the individual hydrocarbon factions or components (e.g. methane, ethane, etc.) in the sample will elute as each reaches its respective boiling point.

The outlet of the capillary column is fluidly connected to one end of a combustion reactor tube which, in turn, is positioned inside the furnace. The reactor tube contains a metal catalyst, e.g. extruded strand(s) of wire (e.g. copper, nickel, and/or platinum). Each component of the sample is combusted in the presence of this catalyst as it passes through the combustion tube to form (a) water and (b) carbon dioxide products which are representative of the particular component (e.g. methane) being combusted. The other end or outlet of the combustion tube is fluidly connected to the flowpath within the water separator where the water is removed from the sample.

The sample then flows through the gas reduction unit (e.g. an "open split") where excess carbon dioxide gas is removed before the sample passes into the isotope ratio mass spectrometer (MS). As will be understood, the MS detects and measures each carbon dioxide isotope as it passes therethrough and generates a signal representative thereof. These signals are then processed by the data processing unit to thereby generate a chromatographic trace or chromatogram having peaks thereon which are representative of the individually measured carbon dioxide isotopes.

In known furnaces of the type described above, the combustion reactor tube is comprised of a relatively large-diameter glass or ceramic tube (i.e. 0.6 mm I.D.). This larger, non-capillary tube introduces a relatively large amount of "dead volume" into flowpath of the sample as the sample passes from the capillary column into the combustion tube. This "dead volume" allows the sample to "spread" out or dissipate which, in turn, causes "broadening" (i.e. decreased resolution) of the respective peaks on the chromatogram thereby adversely affecting the accuracy of the measurements.

In accordance with the present invention, the combustion tube is formed of a clear glass capillary tube having one end connected to the outlet of the GC capillary column and has approximately the same inside diameter as that of the capillary column (e.g. 0.25 mm I.D.) whereby any "dead volume" attributable to the combustion tube is substantially eliminated. The capillary combustion tube is placed within a glass or ceramic tube sheath and is held therein by any appropriate means, e.g. polyimide resin or the like. The other end of the capillary combustion tube is connected to the downstream capillary flowpath leading to the MS. By providing a continuous capillary flowpath between the capillary column of the GC and the MS, any "dead volume" in the sample flowpath is substantially reduced thereby increasing the peak resolution of the measured isotopes.

BRIEF DESCRIPTION OF THE DRAWINGS

The actual operation and apparent advantages of the present invention will be better understood by referring to the drawings, not necessarily to scale, in which like numbers identify like parts and in which.

BEST KNOWN MODE FOR CARRYING OUT THE INVENTION

Figure 1:
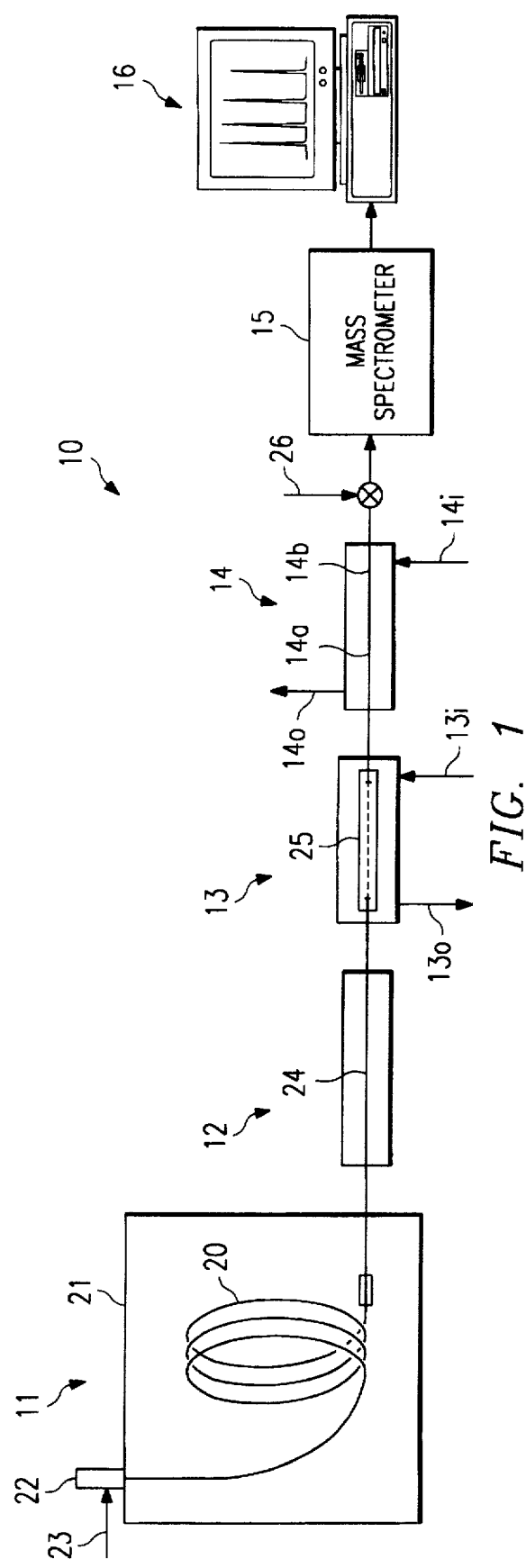
FIG. 1 is a schematical representation of a typical isotope ratio monitoring gas chromatograph-mass spectrometer (irm-GC/MS) unit which is capable of measuring carbon dioxide isotopes of specific organic components in complex GC amenable mixtures.

Referring more particularly to the drawings, FIG. 1 is a schematical representation of a typical isotope ratio monitoring gas chromatograph-mass spectrometer (irm-GC/MS) unit 10 which is capable of measuring the individual carbon dioxide isotopes which, in turn, are produced when the respective components (e.g. methane, ethane, etc.) of a hydrocarbon mixture are combusted in the presence of a metal catalyst. Basically, the irm-GC/MS unit 10 is comprised of a gas chromatograph 11, a combustion reactor or furnace 12, a water separator 13, a gas-reduction unit 14, a mass spectrometer 15, and a data processing unit 16. Each of these components have a flowpath therethrough which are connected to provide a continuous flowpath between GC 11 and spectrometer 15, as will be understood in the art.

The irm-GC/MS unit 10 as described above, is well known and systems of this configuration are commonly used to measure carbon dioxide isotopes in the analysis of complex GC amenable mixtures (e.g. petroleum hydrocarbons). These are all standard and well known, commercially-available components and accordingly each will only be described to the extent necessary to understand the present invention.

For example, GC 11 may be one which is commercially-available (e.g. Hewlett-Packard Model 5890) and which contains a polyimide coated glass capillary column 20 positioned within oven 21. Column 20 is typically formed of a long length (e.g. 15–60 meters) of coiled capillary tubing (e.g. 0.25–0.53 mm I.D.). The GC column typically has an injector port 22 at its inlet. This allows the sample to be introduced into the capillary column 20 by any of a variety of manual or automatic sample injection options.

As will be understood, a carrier gas, e.g. helium or nitrogen, flow into the inlet of injector port 22 through line 23 thereby assisting the sample in transportation through the GC unit 11, as is common in this art. The oven will heat the sample via a systematic temperature ramp following a predetermined heating rate program as the sample passes through column 20 from an initial starting temperature (e.g. 70° C.) to a higher exit temperature (e.g. 300° C.). As the sample passes through and is heated in the GC column, the individual hydrocarbon factions or components (e.g. methane, ethane, etc.) will elute as each reach their respective boiling points, which occurs and is recorded at spaced timed intervals.

The outlet of capillary column 20 is connected to a combustion reactor tube 24 which is positioned inside furnace 12 which, in turn, is typically an electrically-heated, ceramically-insulated housing. Such furnaces are commercially-available, e.g. distributed by Southwest Heater, Dallas, Tex. The reactor tube 24 normally contains a metal catalyst, either in the form of small pellets (e.g. copper) or as an extruded strand(s) of wire 31 (e.g. copper, nickel, and/or platinum) which extends through reactor tube 24.

The sample is heated by furnace 12 to a very high temperature (e.g. 900° C.) as it passes through combustion reactor tube 24. This causes each of the individual hydrocarbon components to undergo combustion which, in the presence of the metal catalyst, forms water and carbon dioxide products which are representative of that particular component (e.g. methane). The outlet of combustion tube 13 is connected to a passage 25 which extends through water separator 13. Preferably, passage 25 is formed of a water-permeable, gas impermeable material (e.g. Nafion tubing, available from Perma Pure Inc., Toms River, N.J.). The water in the sample permeates through tube 25 into the housing of separator 13 and is carried therefrom by a gas (e.g. helium) which, in turn, flow counter-current from inlet 13$i$ to outlet 13$o$.

The sample now flows through gas reduction unit 14 which may be termed an "open split" and basically represents a smaller tube 14$b$ (e.g. 0.10 mm I.D.) telescoped within a larger tube 14$a$ (e.g. 0.32 mm I.D.) wherein gas can "leak" around the tubes and be carried from unit 14 by helium or the like which, in turn, flows in a counter-current manner between inlet 14$i$ and 14$o$. The sample stream then flows into a commercially-available, isotope ratio mass spectrometer 16 (e.g. Model SIRA II, MicroMass, U.K.). A reference gas (i.e. carbon dioxide standard) may also be added to the sample analysis through line 26 as is common in this art.

As will be understood, spectrometer 15 detects and measures each carbon dioxide isotope as that individual carbon dioxide gas passes therethrough and generates a signal representative thereof. These signals are inputted to data processing unit 16 which is programmed to analyze the signals and generate a chromatographic trace having peaks thereon which are representative of the different, measured carbon dioxide isotopes.

In known furnaces 12 of the type described above, the combustion reactor tube 24 comprises a relatively large-diameter glass or ceramic tube (i.e. 0.6 mm I.D.). By passing the sample from the small capillary column 20 (e.g. 0.25 mm I.D.) into the relatively, much larger combustion reactor tube 24 (e.g. 0.6 mm I.D.), a relatively large amount of "dead volume" is inherently introduced into the sample flowpath.

It is believed that this "dead volume" slows up the flow of the sample and allows it to "spread" out or dissipate within the flowpath. This spreading out of the sample before it reaches spectrometer 15 ultimately adversely affects the accuracy of the measurements of the individual carbon dioxide isotopes in the complex mixture. It is surmised that at least some fraction of a particular isotope may lag behind as it passes through spectrometer 15 and is erroneously recorded on the chromatographic trace as being part of the next peak to be measured. This possible overlap of even a minute fraction of adjacent isotopes due to the "broadening" of their respective peaks on the chromatographic trace may, in turn, result in obscuring the point on the curve at which a particular peak actually begins and/or ends. This inability to discern the exact start and/or finish of the respective peaks seriously affects the accuracy of the results derived from the integration of these peaks; i.e. integrating the area under the trace to determine the respective areas under the peaks to arrive at the isotope value for a respective hydocarbon component.

Figure 2:
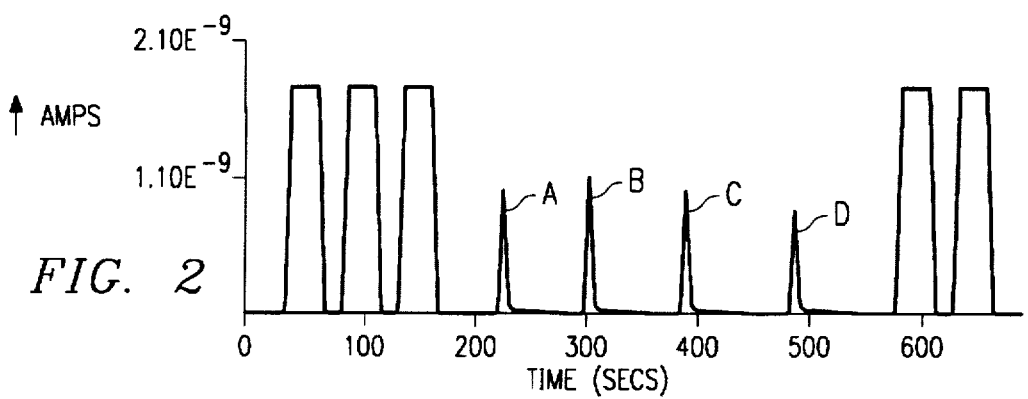
FIG. 2 is a chromatographic trace (or chromatogram) of the type furnished with a typical, prior-art, commercially-available irm-GC/MS having basically the same components of that shown in FIG. 1 illustrating a trace which can be expected when a standard sample of a known hydrocarbon mixture is analyzed with said prior-art irm-GC/MS.
Figure 3:
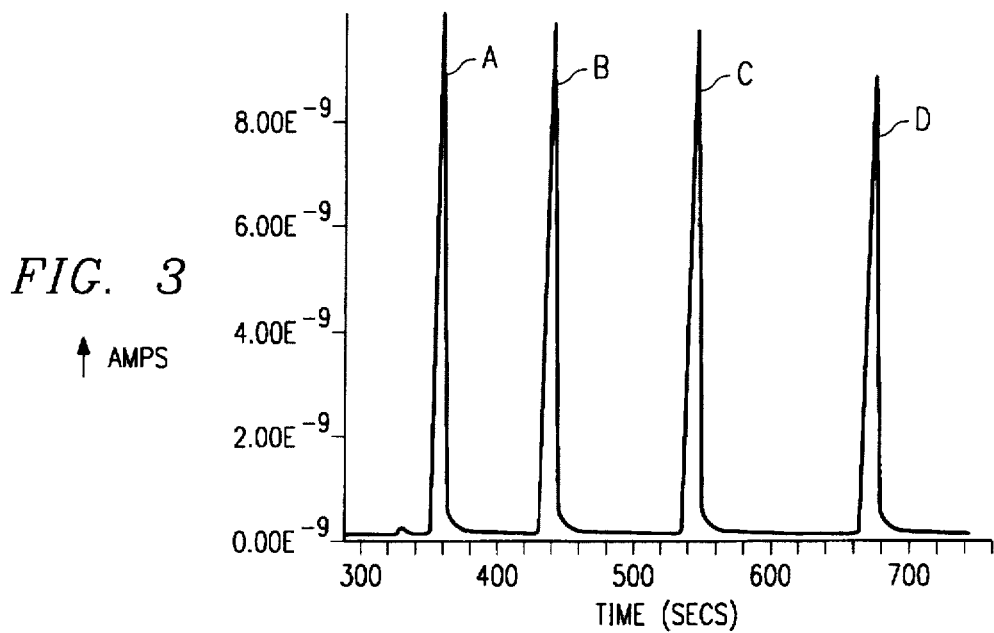
FIG. 3 is a chromatogram of the same standard, known hydrocarbon mixture used to obtain the chromatogram of FIG. 2 when said mixture was actually passed through the said prior-art irm-GC/MS.
Figure 4:
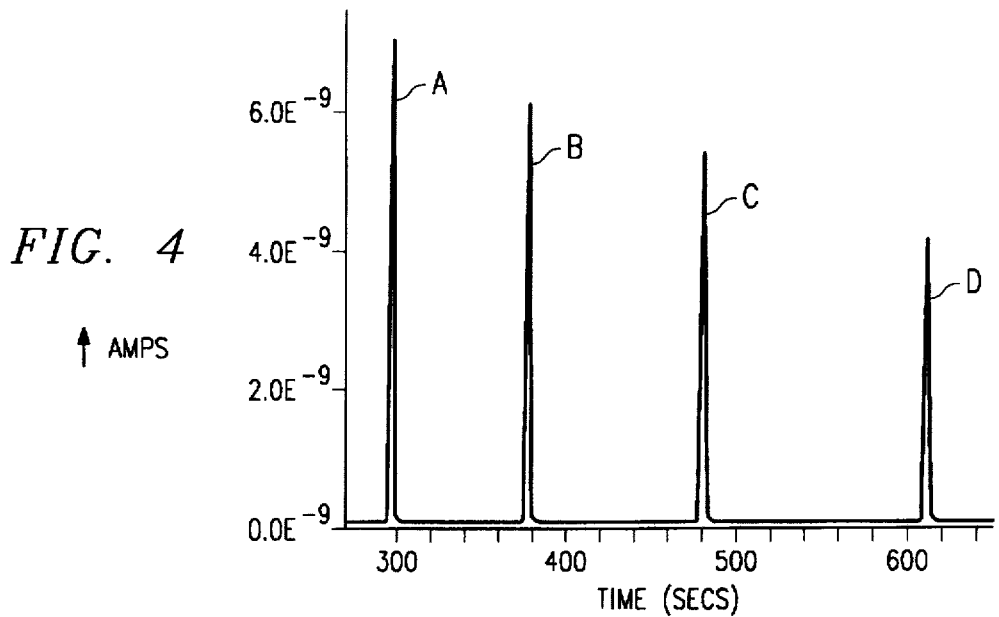
FIG. 4 is a chromatogram of the same standard sample used to obtain the chromatograms of FIGS. 2 and 3 when passed through a irm-GC/MS having the basic components of that shown in FIG. 1 but modified in accordance with the present invention.

Just how the dead volume in the sample flowpath can seriously affect the resolution of the individual peaks on a chromatogram can be seen by considering the traces shown in FIGS. 2–4. FIG. 2 is a chromatogram as shown in the operating manual which, in turn, was furnished with a commercially-available irm-GC/MS unit, the unit having a large, non-capillary combustion tube 24 such as that described above. The chromatogram of FIG. 2 is intended to fairly represent measurements of the respective carbon dioxides isotopes when a standard hydrocarbon sample is measured by that particular irm-GC/MS unit. FIG. 3 illustrates the measurement of these same carbon dioxide isotopes when the same standard sample was actually measured by the same commercial irm-GC-MS unit. It can be seen from these FIGS. that the "peaks" A (Hydrocarbon 1), B (Hydrocarbon 2), C (Hydrocarbon 2), and D (Hydrocarbon 4) on the traces are not well defined in that they all tail off which makes it difficult to identify their exact end points on the respective traces.

Figure 5:
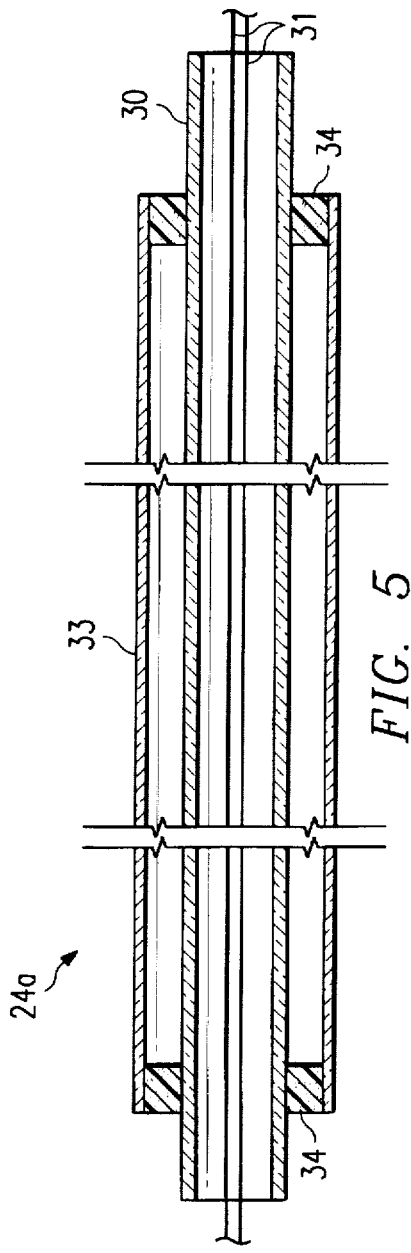
FIG. 5 is an enlarged sectional view of the capillary combustion tube of the present invention.

In accordance with the present invention, the prior-art combustion tube 24 is replaced with a capillary combustion tube 24$a$ (FIG. 5) whereby any "dead volume" attributable to the increased diameter of the previous tube is eliminated. Preferably, a length of polyimide-coated glass capillary tube 30 (e.g. SGE, Austin, Tex.) having basically the same I.D. as that of the capillary column 20 (about 0.25 mm I.D.) is used in forming combustion tube 24$a$.

Since the polyimide coating may be unstable at the elevated temperatures within the furnace, the polyimide coating is removed from tube 30 along that portion of its length which will actually lie within furnace 12, thus leaving a clear, uncoated glass capillary within the furnace. Length (s) of catalytic wire 31 (e.g. copper, nickel, and/or platinum), are inserted into the combustion tube 30 and are sized to extend through that portion of tube 30 which lies within furnace 12. Capillary tube 30 is placed within a glass or ceramic tube sheath 33 for mechanical protection and thermal shielding and is held therein using polyimide resin 34 or the like. The ends of capillary tube 30 are directly connected respectively to capillary GC column 20 and to the capillary flowpath leading to mass spectrometer 15. The capillary-to-capillary connections are made with low dead volume fittings, e.g. SGE, Austin, Tex. (not shown).

By providing a continuous capillary flowpath through irm-GC/MS unit 10, substantial amounts of "dead volume"are eliminated thereby increasing the peak resolution of the measured isotopes. FIG. 4 is a chromatogram wherein the same standard sample as that used for the chromatograms of FIGS. 2 and 3 was passed through a irm-GC/MS unit having the combustion reaction tube 24a of the present invention incorporated therein. It can be seen how each peak (A, B, C, and D) is much sharper when compared to its respective peaks in the preceding chromatograms. The end of each of the sharp peaks can thus be determine more accurately than could be with the prior combustion tubes. This, in turn, greatly improves the accuracy of these measurements and hence, the accuracy of the data.

The above examples serve only to illustrate general irm-GC/MS methodologies and represent the simplest cases possible. GC amenable organic samples such as petroleum hydrocarbon mixtures, in fact, are generally extremely complex, comprising tens to thousands of individual components and requiring state of the art techniques to effect their separation from each other. Seemingly modest improvements in peak resolution actually result in large degrees of separations between individual components facilitating the analysis and interpretation of such complex mixtures with greater confidence and efficacy.

What is claimed is:

1. An isotope ratio monitoring gas chromatograph mass spectrometer (irm-GC/MS) unit for analyzing a gas chromatograph amenable organic sample, said irm-GC/MS unit comprising:

a gas chromatograph (GC) comprising an oven;

a capillary column positioned within said oven and having an inlet adapted to receive said sample;

a furnace having a flowpath therethrough, said flowpath being formed of a capillary combustion tube which is fluidly connected at one end to said capillary column and which has an inside diameter substantially equal to the inside diameter of said capillary column; and a mass spectrometer fluidly connected to the other end of said capillary combustion tube in said furnace.

2. The irm-GC/MS unit of claim 1 wherein said inside diameters of said capillary column and said capillary combustion tube are about 0.25 mm.

3. The irm-GC/MS unit of claim 1 wherein said capillary combustion tube comprises:

a capillary tube of a length sufficient to extend through said furnace;

a metal catalyst positioned within said capillary tube;

a sheath longitudinally extending along said capillary tube; and means for holding said capillary tube within said sheath.

4. The irm-GC/MS unit of claim 3 wherein said capillary tube is a clear glass capillary tube along the portion of its length which extends through said furnace.

5. The irm-GC/MS unit of claim 4 wherein said sheath is a glass tube concentrally positioned over said capillary tube.

6. The irm-GC/MS unit of claim 4 wherein said sheath is a ceramic tube concentrally positioned over said capillary tube.

7. The irm-GC/MS unit of claim 4 wherein said means for holding said capillary tube within said sheath is comprised of polyimide resin.

8. The irm-GC/MS unit of claim 1 including:

a water separator having a capillary flowpath therethrough which has one end fluidly connected to the other end of said capillary combustion tube in said furnace; and a gas-reduction unit having a capillary flowpath therethrough which has one end fluidly connected to the other end of said capillary flowpath through said water separator and which has its other end fluidly connected to said mass spectrometer (MS), whereby there is a continuous capillary flowpath from said inlet of said capillary column of said GC to said MS.

9. In an isotope ratio monitoring gas chromatograph mass spectrometer (irm-GC/MS) unit for analyzing a gas chromatograph (GC) amenable organic sample, said irm-GC-MS unit comprising a gas chromatograph having a capillary column, a furnace, a water separator, a gas-reduction unit, a mass spectrometer (MS), and a data processing unit, the improvement comprising a capillary flowpath from said GC to said MS through which said sample flows from said GC to said MS wherein the inside diameter of said capillary flowpath is substantially equal to the inside diameter of said capillary column.

10. In the irm-GC/MS unit of claim 9 wherein said inside diameters of said capillary flowpath through said furnace and said capillary column in said GC is about 0.25 mm.

11. In the irm-GC/MS unit of claim 9 wherein the said portion of said capillary flowpath passing through said furnace comprises a capillary tube of a length sufficient to extend through said furnace;

a metal catalyst positioned within said capillary tube;

a sheath longitudinally extending along said capillary tube; and means for holding said capillary tube within said sheath.

12. In the irm-GC/MS unit of claim 11 wherein said capillary tube is a clear glass capillary tube along its portion which extends through said furnace.

13. In the irm-GC/MS unit of claim 12 wherein said sheath is a glass tube concentrally positioned over said capillary tube.

14. In the irm-GC/MS unit of claim 12 wherein said sheath is a ceramic tube concentrally positioned over said capillary tube.

15. In the irm-GC/MS unit of claim 12 wherein said means for holding said capillary tube within said sheath is comprised of polyimide resin.

* * * * *